(12) United States Patent
Van Andel

(10) Patent No.: US 7,488,296 B1
(45) Date of Patent: Feb. 10, 2009

(54) MULTIFUNCTIONAL ACTUATOR ROD AND HANDLE FOR PUSHING A DRIVER CABLE OF A BIOPSY GRASPING INSTRUMENT

(76) Inventor: James A. Van Andel, 13933 Islandview Ct., Walnut Grove, CA (US) 95690

( * ) Notice: Subject to any disclaimer, the term of this patent is extended or adjusted under 35 U.S.C. 154(b) by 0 days.

(21) Appl. No.: 11/985,462

(22) Filed: Nov. 15, 2007

(51) Int. Cl.
*A61B 10/00* (2006.01)
(52) U.S. Cl. ..................................... 600/564
(58) Field of Classification Search ......... 600/562–567; 606/142, 205, 207, 170, 174
See application file for complete search history.

(56) References Cited

U.S. PATENT DOCUMENTS 5,308,358 A * 5/1994 Bond et al. .................. 606/205
5,478,350 A * 12/1995 Kratsch et al. ............... 606/205
2005/0277953 A1* 12/2005 Francese et al. ............. 606/142

* cited by examiner

*Primary Examiner*—Max Hindenburg
*Assistant Examiner*—Brian Szmal
(74) *Attorney, Agent, or Firm*—Donald W. Meeker

(57) ABSTRACT

A plastic disposable scissor-action biopsy or grasping tool handle has a standard adapter tube attached to a front arm of the handle. An actuator rod attaches to the handle with the standard biopsy tool driver cable attached to the actuator rod. An actuator rod front tubular portion is slidable within the front handle arm. The actuator rod back portion has an elongated horizontal slot therethrough with a stop pin through the slot attached to a pair of mating stop pin holes within an actuator rod receiving recess in the back arm of the handle. A spring interacts between an actuator rod spring stop and the rear handle arm to regulate bite pressure of the biopsy cutting tool. The back handle arm pushes the driver cable to operate the biopsy cutting tool.

6 Claims, 4 Drawing Sheets

MULTIFUNCTIONAL ACTUATOR ROD AND HANDLE FOR PUSHING A DRIVER CABLE OF A BIOPSY GRASPING INSTRUMENT

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

1. Field of the Invention

The present invention relates to surgical biopsy instruments and particularly to a multifunctional actuator rod for a tissue collecting mechanism which is used with a disposable plastic scissor-type handle, wherein the actuation rod may be disposable and provides the functions of controlling the force applied to the mechanism, limiting and or blocking the flow of blood through the lumen, eliminating rotation to create steering ability, reducing the travel ratio between the handle and the mechanism, keeping the driver wire or cable from kinking, and providing a place to position and fasten the driver wire or cable.

2. Description of Related Art Including Information Disclosed Under 37 CFR 1.97 and 1.98

Flexible medical biopsy and grasping devices are most commonly actuated by pull mechanisms that in turn require risky and bulky scissor links that waste energy, and have limitations that hinder surgeons and technicians in the performance of their task.

U.S. Pat. No. 4,084,594, issued Apr. 18, 1978 to Mosior, claims a surgical instrument having miniature cutting and/or grasping elements at its distal end and having a proximal end portion detachably connected to an operating handle assembly. The handle assembly includes a pair of identical spring-loaded interfitting wing lock members which are capable of being cammed outwardly for readily accepting and coupling to the instrument's proximal end and which are constructed for securely retaining the instrument against accidental release. The handles of the assembly are spring-urged into neutral positions to insure proper positioning of such handles for quick coupling of the instrument and handle assembly.

U.S. Pat. No. 5,009,661, issued Apr. 23, 1991 to Michelson, shows a protective spring mechanism employed to protect the jaws of a surgical rongeur, thereby protecting the fragile parts of the activating mechanism from excessive peak loads and preventing breakage.

U.S. Pat. No. 5,308,358, issued May 3, 1994 to Bond, shows rigid-shaft surgical instruments that can be disassembled for improved cleaning. The invention relates to single-tool surgical instruments, such as scissors or forceps which do not pass through a channel in an operating laparoscope, which contain moving actuator parts at the end of a long slender shaft comprising a tube and a yoke. The actuator is operated by means of a handle assembly, which either forces or retracts an interior rod through a hollow shaft tube. These instruments can be disassembled to remove the interior rod from inside the shaft tube. This allows improved cleaning and removal of blood or tissue residues from the interior rod and shaft tube prior to sterilization, to provide for more effective and reliable sterilization of the components. The assembly includes a union coupling near the handle, which allows the shaft tube to be disengaged from the handle without rotating either the interior rod or the shaft tube. After the shaft tube has been disengaged and pulled away slightly, the shaft and actuator assembly are rotated relative to the handle assembly. This unscrews the actuator assembly from the end of the interior rod. After the interior rod disengages from the actuator assembly, the shaft and actuator are pulled away from the handle assembly and interior rod. This exposes the interior rod and provides open access to the interior of the shaft tube, so that both components can be cleaned to remove any blood or tissue residue prior to sterilization. If desired, the actuator assembly can be removed from the end of the shaft tube, by removing a pivot screw, or by installing the actuator assembly in a shaft yoke device, which can be removed from the end of the shaft tube.

U.S. Pat. No. 2,113,246, issued Apr. 5, 1938 to Wappler, describes endoscopic forceps, which comprise a flexible conduit which removably seats in a scissor-style operating handle.

U.S. Pat. No. 1,127,948, issued Feb. 9, 1915 to Wappler, discloses a cystoscope comprising a handle portion with a scissors grip, a shaft extending from the scissors grip and shaped to extend through a tube, and a nipping end tool actuatable by the scissors handle.

U.S. Pat. No. 4,569,131, issued Feb. 11, 1986 to Falk, indicates a tool having a handle with an interchangeable insert portion mounted on a handle portion which handle portion will actuate a pincher-like tool arrangement on the free end of the insert portion characterized by a locking arrangement for holding the pincher-like tool in a closed position by holding the handle portion in the closed position and a stop arrangement to limit the amount of movement of the pincher-like tool toward the closed position.

U.S. Pat. No. 4,122,856, issued Oct. 31, 1978 to Mosior, puts forth a surgical instrument having a sheath, a grasping and/or cutting jaw assembly at one end of the sheath, a housing at the sheath's opposite end, and a plunger slidably supported by the housing and connected to the jaw assembly by means of an actuator rod extending through the sheath. The housing and plunger portions of the instrument are adapted to be coupled to a scissor-style handle unit, if desired, for manipulation of the instrument and operation of the jaw assembly. The structure and method for facilitating quick removal and replacement of the jaw assembly and actuator rod are disclosed.

Three U.S. Pat. Nos. 5,368,606 issued Nov. 29, 1994, 5,571,137 issued Nov. 5, 1996, and 5,618,303 issued Apr. 8, 1997 to Marlow, concern an endoscopic instrument system which includes a handle portion with a scissors grip, a shaft extending from the scissors grip and shaped to extend through a cannula, and a plurality of disposable end tools, each mountable on the end of the shaft and actuatable by the scissors handle. In a preferred embodiment, the scissors handle actuates a rod extending through the shaft, which is connected to the end tool. The end tool includes a pair of jaws pivotally mounted on the support and connected to a reciprocating stub shaft by links. The stub shaft is connected to the actuating rod of the handle portion so that movement of the scissors handle causes the jaws to pivot relative to each other. The end tool may take the form of a scissor, grasper, biopsy or dissector, depending upon the specific shape of the jaws. An advantage of the invention is that the support of the end tools is made of a relatively inexpensive plastic material such that the end tools may be discarded when the jaws become dull, thus obviating the need for repeated cleaning and sharpening and eliminating the most difficult portion to clean.

U.S. Pat. No. 5,507,297, issued Apr. 16, 1996 to Slater, illustrates an endoscopic instrument having detachable proximal handle and distal portions. The distal assembly includes a tube carrying an end effector and a push rod coupled to the end effector and slidable through the tube. The proximal handle includes a tube sleeve for receiving the tube, an actuator and a latch for coupling the push rod to the actuator. The tube sleeve is provided with a tube lock for holding the tube securely in place and the tube is provided with a circumferential groove for engaging the lock. The latch is spring loaded, hinged, and has an inclined surface for quick coupling with the push rod. The latch also has a mechanism for uncoupling the latch from the push rod. The push rod is provided with a mating tip, which engages the latch so that the actuator causes reciprocal movement of the push rod within the tube to operate the end effector. An axially movable collar on the tube sleeve is used in unlatching, and in one arrangement is also used for rotating the distal assembly.

U.S. Pat. No. 7,025,775, issued Apr. 11, 2006 to Gadberry, is for a surgical instrument includes a removable shaft having a proximal end and a distal end with an operating device disposed at the distal end. A cable assembly is carried by the shaft and extends proximally to a terminus. A handle assembly coupled to the cable assembly concludes a first handle and a second handle. The first handle includes portions configured to receive the terminus and the proximal end of the shaft while portions of the second handle are configured to receive the terminus of the cable assembly. The proximal end of the shaft and the terminus are simultaneously rotatable to cover the proximal end of the shaft to the portions of the first handle and to couple the terminus to the portions of the second handle. The handle assembly can be made sterilizable with a minimum of non-bearing surfaces, while the shaft assembly can be made disposable and interchangeable with various operating devices. An associated method includes the step of releasably locking the shaft assembly to the handle assembly.

U.S. Pat. No. 5,174,300, issued Dec. 29, 1992 to Bales, provides disposable endoscopic or laparoscopic surgical instrument having rotatable end effectors. The medical instruments have end effectors and an end effector actuator apparatus which are rotatable relative to the end effectors, and further comprise an aluminum tube having a longitudinal axis, end effectors, a clevis means, actuating apparatus, and a push rod.

U.S. Pat. No. 5,304,203, issued Apr. 19, 1994 to El-Mallawany, claims tissue extracting forceps, which have been designed for use in laparoscopic surgery. The forceps firmly grasp tissue or organs, which are to be moved or removed during the procedure. The grasping members of the forceps are aligned such that fragmentation damage to the grasped tissue is minimized. The mechanical layout of the forceps allows the user to manipulate the working end for a distance, so that the user's fingers do not get in the way of the surgical procedure. The working end of the forceps is adaptable to be used with grasping members of different shapes, or with disposable cutting instruments. Any of these working ends may be incorporated in the same overall mechanical design.

U.S. Pat. No. 5,569,298, issued Oct. 29, 1996 to Schnell, describes a resposable scissors surgical instrument that has a hollow elongated shaft for insertion into the body, the shaft having a longitudinal axis and supporting a pair of interacting pivotable jaws on its distal end and being connected at its proximal end to a first movable component of an operating handle, with a reciprocable rod located within the shaft. The rod is connected to a second movable component of the handle for reciprocation within the shaft when the first and second components are moved relative to each other. The jaws are pivotally connected by a pivot pin supported on the shaft transversely to the axis. Each of the jaws has a proximal end extending proximally from the pivot pin. Each of the proximal ends is provided with an elongated opening therethrough, each the openings forming an elongated slot oriented at an oblique angle relative to the longitudinal axis of the shaft. The reciprocable rod has a distal end extending into each slot whereby reciprocation of the rod causes the jaws to open and close.

U.S. Pat. No. 5,290,308, issued Mar. 1, 1994 to Knight, discloses a lightweight endoscopic instrument, which has a flushing port with a check valve assembly therein. The check valve retains carbon dioxide, which is used during endoscopic procedures. Upon removal of the instrument, a pressurized fluid can be connected to the flush port, with internal seals directing the pressurized fluid through an annular space between the stem of the instrument and a central actuating rod or element so that any tissue or blood which may have entered into such annular space is flushed out the distal end of the instrument. The instrument features a knob allowing it to rotate on its longitudinal axis while having a handle that can be held in a fixed position by the surgeon. An index mechanism is provided to audibly and/or visually give an indication at preset increments of rotation. The instrument is lightweight to decrease fatigue and is simply and economically constructed.

U.S. Pat. No. 5,718,714, issued Feb. 17, 1998 to Livneh, indicates a surgical instrument with a removable shaft assembly. The surgical instrument shaft assembly includes a drive shaft having an actuatable working member at one end and a connecting member at its other end. The drive shaft has formed thereon a reaction member having a preselected geometrical shape. The reaction member is adapted to removeably operatively connect with a receiving member forming a reacting support. A driving force applied to the drive shaft reacts with the reacting support developing a reaction force to actuate the actuatable working member in a predetermined direction. The surgical instrument further includes a handle assembly which for removeably supporting the shaft assembly. The handle assembly has a first end which defines a receiving member to removeably operatively connect with the reaction member to define the reaction support. The handle assembly includes a releasable coupling member which releasably connects with the connecting member. A rotary member is provided which permits rotation of the elongated housing, shaft assembly and actuatable working member. A locking member is provided to inhibit rotation of the drive shaft when the actuatable working member is actuated.

U.S. Pat. No. 5,496,347, issued Mar. 5, 1996 to Hashiguchi, puts forth a surgical instrument for treatment in the body cavity, in which an open-close member for treatment is rockably mounted by of a pivot pin on the distal end portion of a sheath to be inserted into the body cavity, and is connected to the distal end of a rod passed through the sheath, by a cam mechanism including a cam groove and a cam pin in engagement therewith. As the rod is moved by an operating handle, the cam mechanism is activated to open and close the open-close member for treatment. The component members of the cam mechanism have external shapes such that those portions on the proximal end side of the position near the pivot pin do not project from the sheath in every operating state.

U.S. Pat. No. 5,527,339, issued Jun. 18, 1996 to Koscher, concerns a surgical instrument with two elements sliding into one another has at least one jaw part connected with a sliding element. Both elements are connected with one another detachably by means of a catch device. A distance between the end of a sliding element and the jaw part is variable, but is invariable when at least one jaw part is fixed.

U.S. Pat. No. 6,752,823, issued Jun. 22, 2004 to Prestel, illustrates surgical forceps that include a forceps jaw, with a handle consisting of two grip parts with which the one first grip part is connected to a forceps housing and the other second grip part is pivotable for opening and closing the jaw mouth, with an adjustment rod which is distally and proximally adjustable for opening and closing the jaw mouth and whose proximal end has a connection to a limb of the two limbed second grip part, and with at least one would spring element as an overload protection against the breakage of jaw parts. A particularly effective overload protection, a simple forceps construction and a small constructional size of the forceps are achieved according to the invention in that the spring element consists of a flat material wound in a serpentine manner with windings lying in one plane.

What is needed is a new actuator rod and plastic scissor-type handle for biopsy forceps, which interfaces with the old biopsy mechanism to push the driver cable rather than pulling it to solve a number of problems that the old device was not able to address due to the pulling limitations of the durable metal handle configuration.

BRIEF SUMMARY OF THE INVENTION

An object of the present invention is to provide an activating rod for pushing the driver cable and new plastic disposable scissor-action handle for biopsy forceps, which interfaces with the old biopsy jaw mechanism to solve a number of problems that the old device was not able to address due to the limitations of the durable metal handle configuration wherein the improved biopsy tool of the present invention allows the manufacture of a forward pushing mechanism that overcomes all the issues that the current (pull) mechanism seeks to avoid, wherein a push forward actuator is particularly suited for biopsies or grasping of moving organs such as hearts and lungs, and comprises a multifunctional activator rod to overcome all of the issues and to produce a simple, safe and reliable device.

In brief, the present invention comprises a plastic disposable biopsy tool handle with a scissor action having a standard adaptor tube attached to a front arm of the handle to attach a ridged or flexible shaft and an actuator rod attached to the biopsy tool handle with the standard driver cable of the biopsy tool attached to the actuator rod. The actuator rod comprises a front tubular portion slidable within the front handle arm and a back portion having an elongated horizontal slot therethrough with a stop pin through the slot attached to a pair of mating stop pin holes within an actuator rod receiving recess in the back arm of the handle, so that squeezing the biopsy tool handle together causes the back biopsy tool actuator arm to move the spring which in turn presses against the spring stop of the actuating rod moving the actuator rod forward thereby pushing the driver cable through the biopsy tool front actuator arm and through the biopsy tube to activate the biopsy cutting tool, the tubular portion protecting the driver cable from collapsing under forward pressure on the driver cable. The actuator rod further comprises a spring stop having a spring resting against the spring stop, the spring interacting between the spring stop and the rear biopsy tool actuator arm to regulate bite pressure of the biopsy cutting tool to protect both the cutting edge of the biopsy cutting tool and safeguard all unions and connections from breakage. The length of the horizontal slot reduces the effect of the greater travel of the biopsy tool activating arms of the handle to interact effectively with the limited travel of the other working components and regulates the ratio of travel between the biopsy tool handle and the other moving parts of the biopsy tool in cooperation with the spring to protect the biopsy cutting tool from unsafe pressure and to eliminate rotation of the actuator rod to provide greater steering ability.

The present invention is a device, hereafter named a multifunctional actuation rod, which when it is placed into its companion receiving handle fulfills a unique number of necessary functions. The multifunctional actuation rod must control the force applied to the mechanism, limit and or block the flow of blood through the lumen, eliminate rotation to create steering ability, reduce the travel ratio between the handle and the mechanism, keep the driver cable from kinking, and provide a place to position and fasten the driver wire or cable. When the multifunctional rod is secured in a scissor-like handle it is able to deliver the six functions above safely and reliably. As presented it is both unique and novel as it enables function, control and direction of forward pushing flexible devices when used in the human body.

The actuator rod attached to the biopsy tool handle performs a plurality of functions that the biopsy tool handle cannot perform by itself. These features in combination enable the device to protect the patient, the operator, and the manufacturer from adverse consequences by establishing and regulating the complex abilities of the device as it interfaces with the operator and the patient.

wherein the actuation rod may be disposable and provides the functions of controlling the force applied to the mechanism, limiting and or blocking the flow of blood through the lumen, eliminating rotation to create steering ability, reducing the travel ratio between the handle and the mechanism, keeping the driver wire or cable from kinking, and providing a place to position and fasten the driver wire or cable.

BRIEF DESCRIPTION OF THE SEVERAL VIEWS OF THE DRAWINGS

These and other details of my invention will be described in connection with the accompanying drawings, which are furnished only by way of illustration and not in limitation of the invention, and in which drawings.

DETAILED DESCRIPTION OF THE INVENTION

In FIGS. 1-8, a multifunctional biopsy tool actuator rod 20 and handle 30 device 10 uniquely performs the functions necessary to safely and effectively operate a flexible medical device, a biopsy tool that utilizes a push mode of operation.

Figure 3:
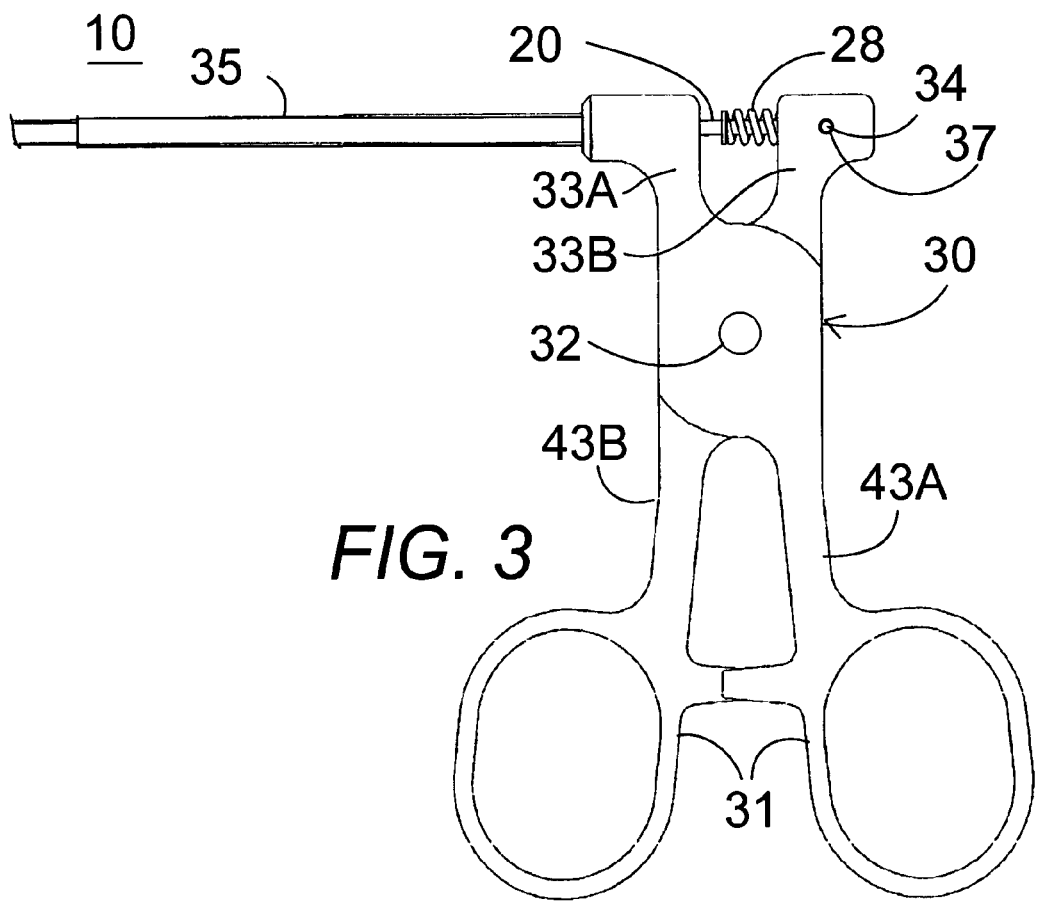
FIG. 3 is a side elevational view of the actuator rod of FIG. 1 installed in the biopsy tool handle of the present invention.
Figure 5:
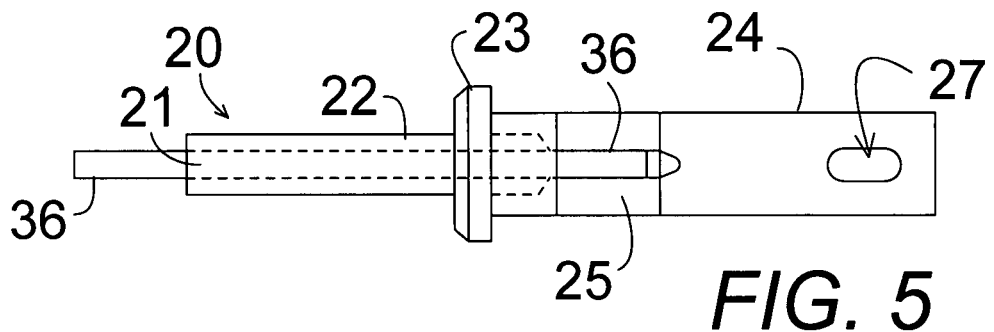
FIG. 5 is a top plan view of a preferred embodiment of the actuator rod of the present invention showing a cylindrical mounting end and the driver cable inserted in the actuator rod.
Figure 6:
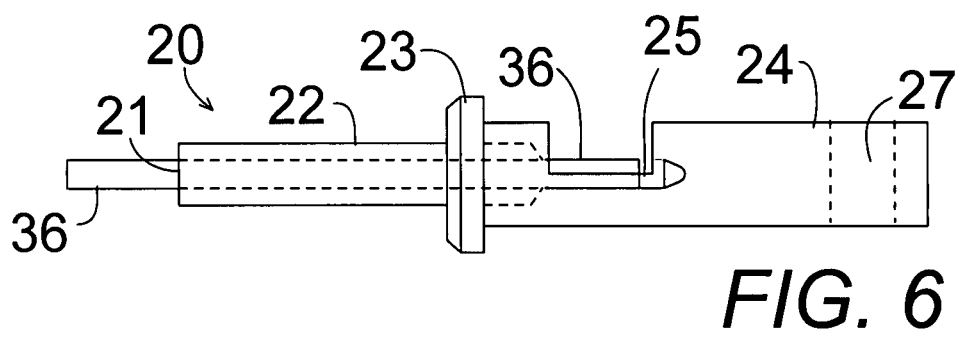
FIG. 6 is a side elevational view of the preferred embodiment of the actuator rod of FIG. 5.
Figure 7:
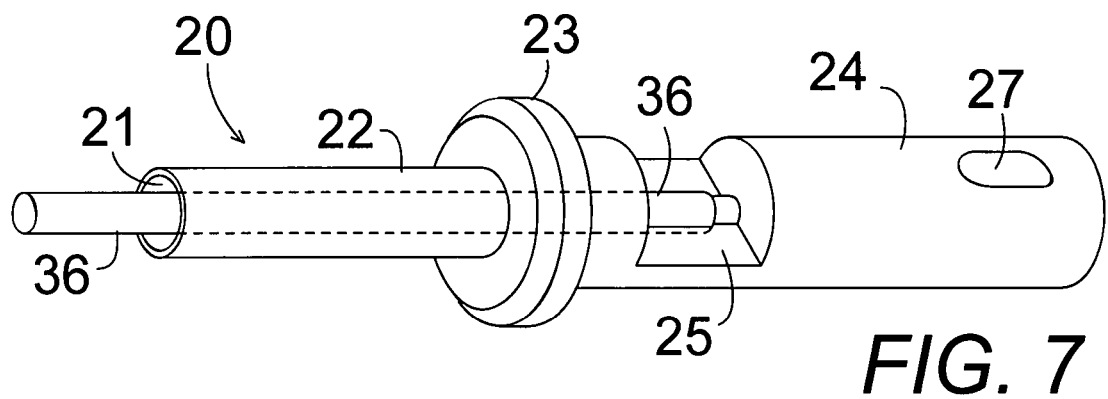
FIG. 7 is a perspective view of the preferred embodiment of the actuator rod of FIG. 5.
Figure 8:
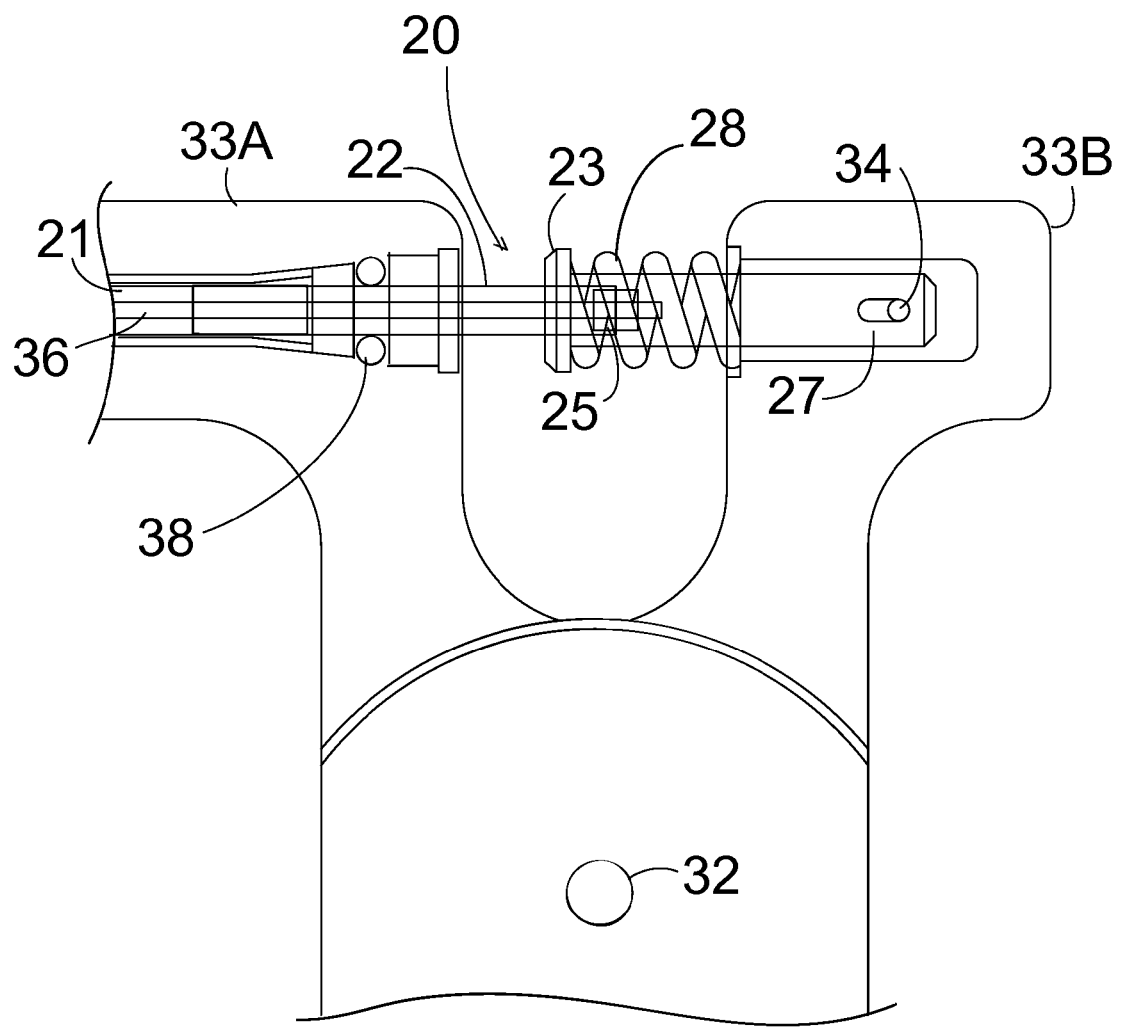
FIG. 8 is a partial side elevational view of the preferred embodiment of the actuator rod of FIG. 5 installed on the biopsy tool handle of the present invention.

In FIGS. 3, 5, and 8, the biopsy tool handle 30 comprising two rigid elongated members interconnected by a pivot mechanism 32, such as a pivot pin, to form a pair of lower hand grasping leg portions comprising a front hand grasping leg portion 43B and a back hand grasping leg portion 43A, and a pair of upper biopsy tool actuator arms comprising a front biopsy tool actuator arm 33A extending from the back hand grasping leg portion 43A and a back biopsy tool actuator arm 33B extending from the front hand grasping leg portion 43B so that squeezing the hand grasping leg portions 43A and 43B moves the tool actuator arms 33A and 33B toward each other. The front biopsy tool actuator arm 33A further comprises a means for securing an adapter tube 35 therein, and the back biopsy tool actuator arm 33B further comprises at least one horizontal opening 37 to admit a pin 34 therein.

In FIGS. 1, 2, and 5-7, the actuator rod 20 comprises a front tubular portion 22 slidable within the front biopsy tool actuator arm 33A. A driver cable 36 extends through a tubular opening 21 in the tubular portion 22, the driver cable 36 extending through the adapter tube 35 and attached to the biopsy cutting tool 40 at a distal end to activate the biopsy cutting tool. A proximal end of the driver cable 36 is attached to the actuator rod 20 at a proximal end in a machined or formed platform notch 25 with a cable recess 21A cut into the actuator rod by welding the proximal end of the driver cable to the actuator rod.

Figure 4:
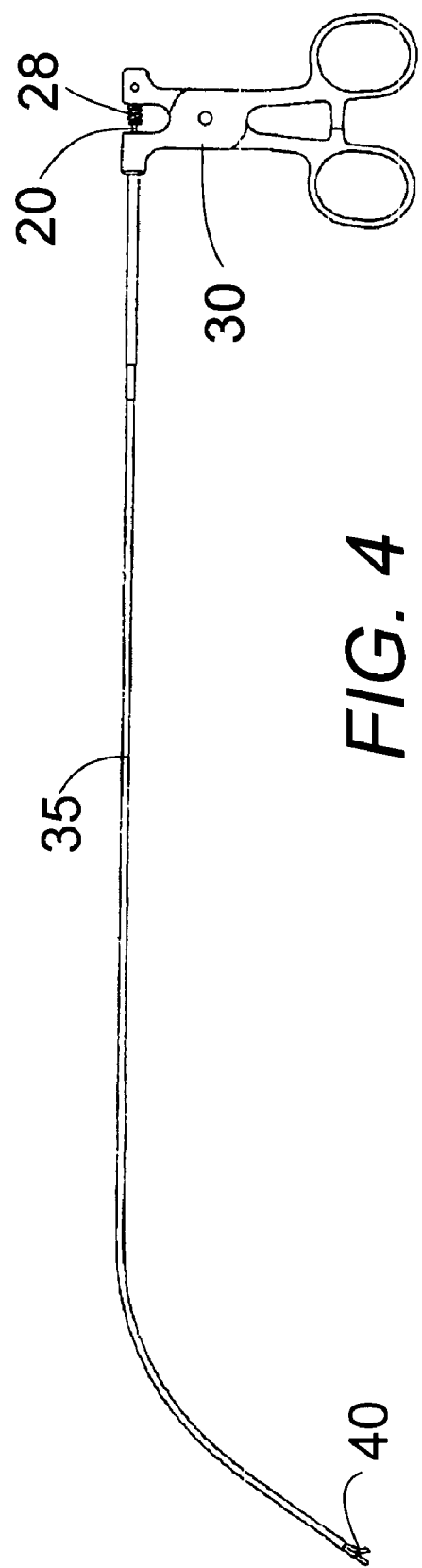
FIG. 4 is a side elevational view of the actuator rod installed in the biopsy tool handle of FIG. 3 further showing the biopsy tube and biopsy cutting tool of the complete instrument.

In FIGS. 3, 4, and 8, squeezing the biopsy actuator tool leg portions 43A and 43B together causes the back biopsy tool actuator arm 33B to push the driver cable 36 through the biopsy tool front actuator arm 33A and through the adapter tube 35 to activate the biopsy cutting tool 40. The tubular portion 22 protects the driver cable 36 from collapsing under the forward pressure on the driver cable 36. A spring 28 rests against a spring stop 23 on the actuator rod 20, the spring 28 interacting between the spring stop 23 and the rear biopsy tool actuator arm 33B to regulate bite pressure of the biopsy cutting tool 40 to protect both the cutting edge of the biopsy cutting tool and safeguard all unions and connections from breakage.

The actuator rod 20 has an elongated horizontal slot 27. A pin 34 inserted between the stop pin holes 37 in the back biopsy tool actuator arm 33B for a connection therebetween. The horizontal slot 27 is elongated in the direction of travel of the driver cable 36 so that the length of the horizontal slot 27 reduces the effect of the greater travel of the biopsy tool activating arms 33A and 33B of the handle 30 to interact effectively with the limited travel of the other working components and regulates the ratio of travel between the biopsy tool handle 30 and the other moving parts of the biopsy tool in cooperation with the spring 28 to protect the biopsy cutting tool 40 from unsafe pressure and to eliminate rotation of the actuator rod 20 to provide greater steering ability.

The tubular portion 22 comprises a smooth portion to provide a surface on which to position a seal 38 to reduce or eliminate leakage of blood through the tubular portion.

The biopsy tool handle 30 is preferably fabricated of a sterile disposable plastic and the actuator rod 20 is disposable to help insure a sterile operating environment.

Figure 1:
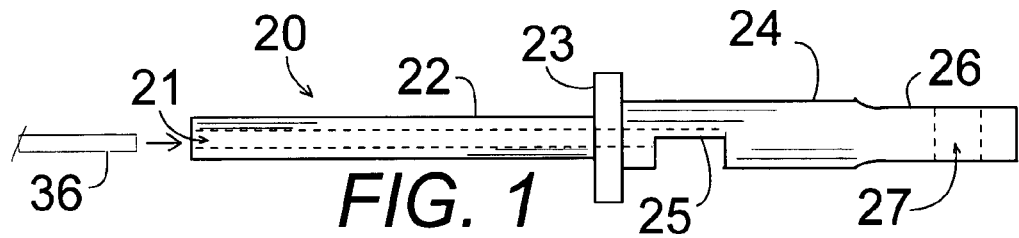
FIG. 1 is a top plan view of the actuator rod of the present invention showing flat side walls on the mounting end and the driver cable aligned for insertion into the tubular portion.
Figure 2:
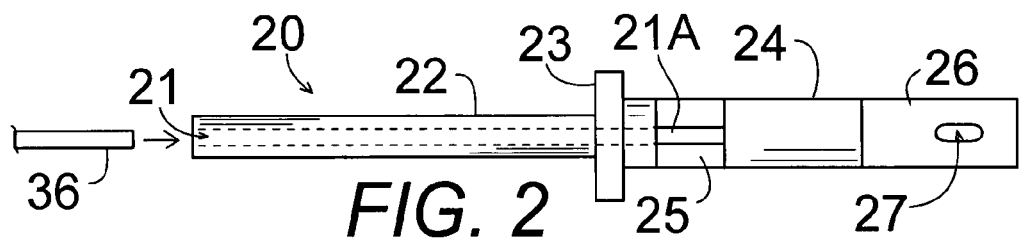
FIG. 2 is a side elevational view of the actuator rod of FIG. 1 showing the driver cable aligned for insertion.

In FIGS. 1-3, the back biopsy tool actuator arm 33B has a vertical slot therein with a pair stop pin holes 37 to receive the pin 34 therein, and a back end of the actuator rod is structured with two vertical side faces 26 to fit within the vertical slot of the back biopsy tool actuator arm.

In FIGS. 5-9, the back biopsy tool actuator arm 33B has a cylindrical opening therein with a pair of stop pin holes 37 to receive the pin therein, and a back end 24 of the actuator rod is cylindrical to fit within the cylindrical opening of the back biopsy tool actuator arm.

It is understood that the preceding description is given merely by way of illustration and not in limitation of the invention and that various modifications may be made thereto without departing from the spirit of the invention as claimed.

What is claimed is:

1. A multifunctional biopsy grasping tool actuator rod and handle device that uniquely performs the functions necessary to safely and effectively operate a flexible medical device that utilizes a push mode of operation, the device comprising:

a biopsy tool handle comprising two rigid elongated members interconnected by a pivot mechanism to form a pair of lower hand grasping leg portions comprising a front hand grasping leg portion and a back hand grasping leg portion, and a pair of upper biopsy tool actuator arms comprising a front biopsy tool actuator arm extending from the back hand grasping leg portion and a back biopsy tool actuator arm extending from the front hand grasping leg portion so that squeezing the hand grasping leg portions moves the tool actuator arms toward each other, the front biopsy tool actuator arm further comprising a means for securing a biopsy tube therein, and the back biopsy tool actuator arm further comprising at least one opening to admit a pin therein;

an actuator rod attached to the biopsy tool handle, the actuator rod comprising a front tubular portion slidable within the front biopsy tool actuator arm; a driver cable extending through the tubular portion, the driver cable extending through the biopsy tube and attached to the biopsy cutting tool at a distal end to activate the biopsy cutting tool and attached to the actuator rod at a proximal end, so that squeezing the biopsy actuator tool leg portions together causes the back biopsy tool actuator arm to push the driver cable through the biopsy tool front actuator arm and through the biopsy tube to activate the biopsy cutting tool, the tubular portion protecting the driver cable from collapsing under forward pressure on the driver cable; a spring stop and a spring resting against the spring stop, the spring interacting between the spring stop and the rear biopsy tool actuator arm to regulate bite pressure of the biopsy cutting tool to protect both the cutting edge of the biopsy cutting tool and safeguard all unions and connections from breakage; the actuator rod having an elongated horizontal slot, a stop pin inserted between the horizontal elongated slot and the at least one stop pin hole in the back biopsy tool actuator arm for a limited length slidable connection therebetween, the horizontal slot elongated in the direction of travel of the driver cable so that the length of the horizontal slot reduces the effect of a greater travel of the biopsy tool activating arms of the handle to interact effectively with the limited travel of the other working components and regulates a ratio of travel between the biopsy tool handle and other moving parts of the biopsy tool in cooperation with the spring to protect the biopsy cutting tool from unsafe pressure and to eliminate rotation of the actuator rod to provide greater steering ability;

wherein the actuator rod further comprises a platform notch cut into the actuator rod for welding the proximal end of the driver cable to the actuator rod.

2. The device of claim 1 wherein the tubular portion comprises a smooth portion to provide a surface on which to position a seal to reduce or eliminate leakage of blood through the tubular portion.

3. The device of claim 1 wherein the biopsy tool handle is fabricated of a disposable plastic to help insure a sterile operating environment.

4. The device of claim 1 wherein the actuator rod is disposable to help insure a sterile operating environment.

5. The device of claim 1 wherein the back biopsy tool actuator arm has a vertical slot therein with a pair of mating stop pin holes to receive the stop pin therein, and a back end of the actuator rod is structured with two vertical side faces to fit within the vertical slot of the back biopsy tool actuator arm.

6. The device of claim 1 wherein the back biopsy tool actuator arm has a cylindrical opening therein with a pair of mating stop pin holes to receive the stop pin therein, and a back end of the actuator rod is cylindrical to fit within the cylindrical opening of the back biopsy tool actuator arm.

* * * * *